(12) United States Patent
Wegener et al.

(10) Patent No.: US 9,381,001 B2
(45) Date of Patent: Jul. 5, 2016

(54) TISSUE SPLITTING BIOPSY NEEDLE

(71) Applicant: EPITOME PHARMACEUTICALS LIMITED, San Diego, CA (US)

(72) Inventors: Paul T. Wegener, San Diego, CA (US); Ryochi Enishi, Gunma (JP); Saverio Bettuzzi, Montecchio Emilia (IT); Takeyoshi Sakashita, Tochigi (JP)

(73) Assignee: EPITOME PHARMACEUTICALS LIMITED, San Diego, CA (US)

( * ) Notice: Subject to any disclaimer, the term of this patent is extended or adjusted under 35 U.S.C. 154(b) by 0 days.

(21) Appl. No.: 14/707,994

(22) Filed: May 8, 2015

(65) Prior Publication Data

US 2015/0238173 A1    Aug. 27, 2015

Related U.S. Application Data

(63) Continuation of application No. 12/738,238, filed as application No. PCT/US2008/081059 on Oct. 24, 2008, now abandoned.

(60) Provisional application No. 60/982,686, filed on Oct. 25, 2007.

(51) Int. Cl.
*A61B 10/00* (2006.01)
*A61B 10/02* (2006.01)
*A61B 17/32* (2006.01)

(52) U.S. Cl.
CPC ......... *A61B 10/0266* (2013.01); *A61B 10/0275* (2013.01); *A61B 10/0283* (2013.01); *A61B 17/32002* (2013.01); *A61B 2010/0208* (2013.01); *A61B 2010/0225* (2013.01); *Y10T 83/207* (2015.04); *Y10T 83/929* (2015.04)

(58) Field of Classification Search
CPC ........... A61B 10/0266; A61B 10/0275; A61B 10/0283; A61B 2010/0225; A61B 17/32002
See application file for complete search history.

(56) References Cited

U.S. PATENT DOCUMENTS

| | | | |
|---|---|---|---|
| 5,027,827 A | 7/1991 | Cody | |
| 5,415,182 A | 5/1995 | Chin et al. | |
| 5,823,971 A | 10/1998 | Robinson et al. | |
| 5,830,153 A * | 11/1998 | Kass ................. | A61B 10/0275 600/567 |
| 5,885,226 A | 3/1999 | Rubinstein et al. | |
| 5,944,673 A | 8/1999 | Gregoire et al. | |
| 5,971,939 A | 10/1999 | DeSantis et al. | |

(Continued)

FOREIGN PATENT DOCUMENTS

| | | |
|---|---|---|
| EP | 1545318 | 6/2005 |
| WO | 2007/021903 | 2/2007 |
| WO | 2007/021905 | 2/2007 |

OTHER PUBLICATIONS

Ursus Medical, "The Rotex Screw Needle Biopsy Instrument", Usus Medical AB, Stockholm, Sweden.

*Primary Examiner* — Devin Henson
(74) *Attorney, Agent, or Firm* — Fish & Tsang, LLP

(57) ABSTRACT

Tissue splitting biopsy devices and methods use a needle portion and a sheath portion that are configured such as to allow simultaneous sectioning of a tissue to produce two tissue samples with corresponding surfaces using motion of the needle portion relative to the sheath portion. Most preferably, the needle portion has a chisel blade tip and at least two cavities opposite to each other and at the same distance from the tip, while the sheath portion has a sharpened front edge.

15 Claims, 3 Drawing Sheets

(56) References Cited

U.S. PATENT DOCUMENTS

| | | | |
|---|---|---|---|
| 6,027,458 A * | 2/2000 | Janssens | A61B 10/0275 600/567 |
| 6,149,607 A | 11/2000 | Simpson et al. | |
| 6,530,891 B2 | 3/2003 | Miller | |
| 6,986,748 B2 * | 1/2006 | McAlister | A61B 10/0266 600/564 |
| 7,137,956 B2 | 11/2006 | Nishtalas et al. | |
| 7,276,032 B2 | 10/2007 | Hibner | |
| 2003/0191413 A1 | 10/2003 | Damarati | |
| 2008/0114265 A1 | 5/2008 | Tarter et al. | |
| 2008/0300506 A1 * | 12/2008 | McIntyre | A61B 10/0275 600/566 |

\* cited by examiner

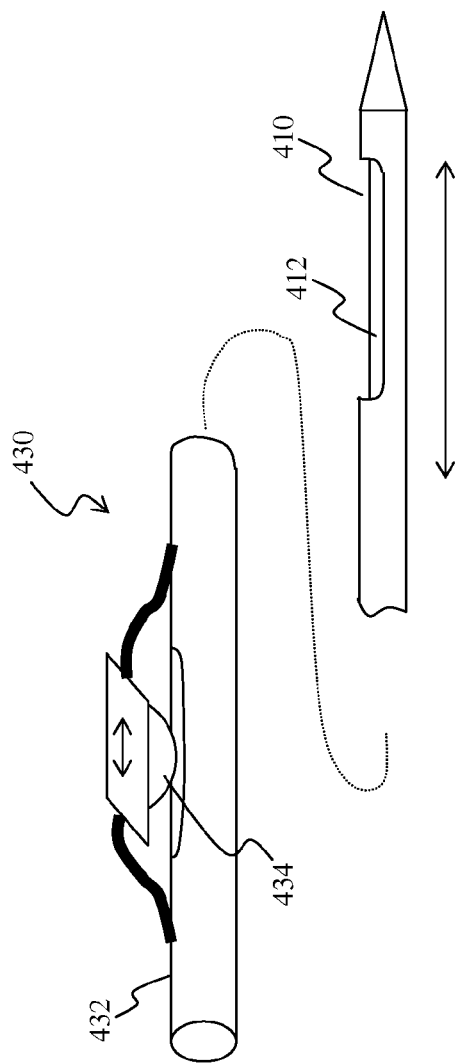
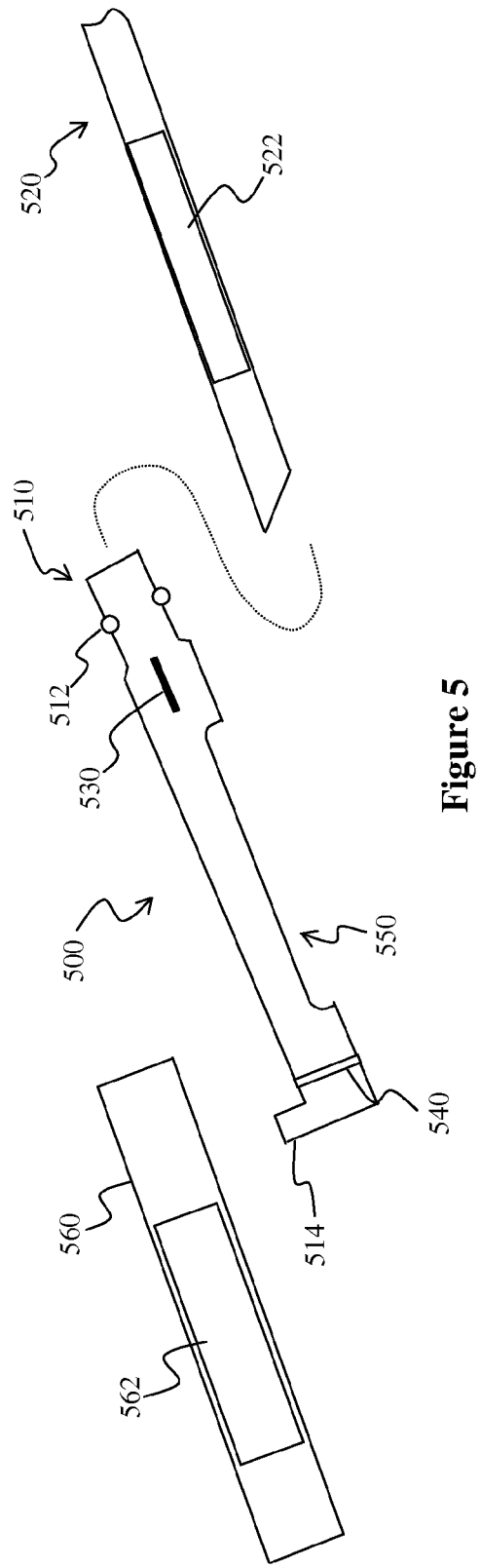
Figure 4
Figure 5

TISSUE SPLITTING BIOPSY NEEDLE

This application is a continuation of U.S. application Ser. No. 12/738,238 filed on Oct. 24, 2008, which is a U.S. national phase application based on PCT/US2008/081059 entitled TISSUE SPLITTING BIOPSY NEEDLE filed on Oct. 24, 2008, and claims priority to U.S. provisional application 60/982686, filed Oct. 25, 2007, and which is incorporated by reference herein.

FIELD OF THE INVENTION

The field of the invention is medical devices, especially as it relates to biopsy needles that produce multiple adjacent tissue samples.

BACKGROUND

Biopsies are often indispensable tools for accurate diagnosis and/or staging of a disease as blood-based tests typically provide only indirect evidence of tissue status, and current imaging analysis often lacks sufficient resolution and information density.

Most commonly, a biopsy is performed using a biopsy gun in which one or more needles are advanced into the target tissue, typically under ultrasound or MRI guidance. A typical biopsy needle and gun is described in U.S. Pat. No. 5,971,939. Where desired, sample acquisition and movement may be assisted using vacuum in the needle as illustrated in U.S. Pat. No. 5,027,827. These and all other extrinsic materials discussed herein are incorporated by reference in their entirety. Furthermore, where a definition or use of a term in an incorporated reference is inconsistent or contrary to the definition of that term provided herein, the definition of that term provided herein applies and the definition of that term in the reference does not apply. A core of tissue is then removed along with the biopsy needle, and the core is immersed in a fixative or frozen after removal from the needle.

The core is subsequently embedded in paraffin and cut, or cryo-sectioned for mounting on a microscope slide prior to staining, nucleic acid analysis, or other analysis. Unfortunately, the processing steps for visual analysis of tissue (e.g., fixation, paraffin embedding, and staining) and molecular biological analysis of tissue (e.g., in-situ PCR, fluorescence in-situ hybridization, etc.) are in many cases incompatible and thus require multiple tissue samples to be taken from the area under investigation.

Multiple-sample biopsies can be performed in numerous manners using certain devices and methods known in the art. For example, U.S. Pat. No. 5,415,182 describes a biopsy gun in which an array of needles is fired into the suspect tissue. Alternatively, as disclosed in EP 1 545 318 B1, a single biopsy needle has a plurality of separate sample cavities to allow sampling in multiple locations. In still further known devices, multiple radially arranged windows in a cannula in conjunction with an internal cutter are used to generate a plurality of samples in proximal location to each other as taught in U.S. Pat. No. 5,944,673. Alternatively, multiple samples in relative proximity can be obtained using a system in which a cannula has multiple openings and in which a spiral blade is advanced to section the samples from the tissue as described in U.S. Pat. No. 6,530,891. While such devices advantageously allow collection of multiple samples from a single area, various disadvantages nevertheless remain. For example, where a malignancy is relatively small or distributed irregularly across a tissue (e.g., various malignancies in the prostate), the collected samples often fail to be co-located in the same area of interest. Therefore, the above devices often fail to provide consistent and representative samples.

The same difficulties exist in still further known devices where multiple biopsies can be taken serially through a single sample window or needle with a flexible retractable tip cover as disclosed in U.S. Pat. No. 6,149,607 and WO2007/021903A2, and U.S. Pat. No. 7,137,956, respectively. While such devices allow collection of multiple samples in multiple areas of interest, samples produced with these devices typically fail to produce tissue of the same area of interest.

To overcome at least some of the difficulties associated with multiple samples from the same area, certain biopsy devices have been described in which a sample is cut from the tissue of interest via a cannula or needle in which the tissue is further sectioned as the cannula or needle advances. For example, FIG. 6 in U.S. Pat. No. 5,823,971 illustrates a cannula in which a cutting wire is placed across the front cutting edge of a round cannula. In such devices, the tissue core is split in the cannula as the cannula advances and cuts the core from the tissue via rotation. Similarly, U.S. Pat. App. No. 2008/0114265 teaches an open-ended needle tip that cuts a cylinder of tissue as the needle advances through the tissue. An internal separator structure then splits the cylinder and maintains the split products in separate cavities from which they can be removed by removing an outer cover sheath that covers the cavities when the needle is inserted into the area of interest. While such devices and methods at least conceptually produce two samples from the same location, numerous difficulties nevertheless remain. Most significantly, as the tissue is forced through the lumen of the cannula or needle, tissue distortion due to friction along the inside of the cannula or needle, and/or compression due to the added volume of the blade/separator structure will occur and lead to loss of tissue and tissue integrity, which is particularly pronounced in the device of the '265 application as the inner lumen is significantly smaller than the cutting tip lumen.

In an attempt to avoid such drawbacks, a biopsy core can be split after removal from the needle in longitudinal direction before processing. However, such post-harvest splitting requires considerable expertise and equipment typically not available in the clinic at which the biopsy is taken. Moreover, even where great care is taken to split the biopsy core equally, consistent splitting is rarely achieved throughout the entire length of the core.

Therefore, while numerous devices and methods for biopsies are known in the art, all or almost all of them suffer from one or more disadvantages. Most significantly, correlation of the corresponding areas is typically not possible as non-adjacent surfaces are generally obtained in such devices and methods. Consequently, there is still a need to provide improved devices and methods for biopsies.

SUMMARY OF THE INVENTION

The inventive subject matter is drawn to various devices and methods to produce biopsy samples having corresponding surfaces in a manner that helps preserve tissue integrity and that allows for manual or automated sampling. In most preferred aspects of the inventive subject matter, a biopsy device has a needle portion that upon movement of the needle portion through the tissue incises the tissue to so produce or initiate formation of corresponding tissue surfaces, which are then received in respective cavities in the needle portion. A sheath portion having a sharpened front end then severs tissue samples carrying the corresponding surfaces from the tissue by moving along the needle portion (in sliding and/or rotating motion) to so secure the samples in the device for retrieval.

In one especially preferred aspect, a biopsy device includes a needle portion and a sheath portion, wherein the needle portion has a closed incising tip and further has two cavities on opposite sides positioned such that at least part of each cavity has the same distance from the tip, and wherein the sheath portion has a sharpened front edge that allows sectioning of respective tissue that is at least partially disposed in the two cavities.

Most typically, the closed incising tip is configured as a chisel blade, and/or has an incising proximal end and a distal end in which the distal end is thinner than a portion of the tip between the proximal end and the distal end. Where desired, the tip may comprise a slit in longitudinal direction to accommodate at least part of a blade. It is further generally preferred that at least 70% of the longitudinal dimension of the two cavities have the same distance from the tip. Furthermore, it should be appreciated that while the two cavities are generally separate cavities, the cavities may also form a contiguous opening through the needle portion. Additionally, the needle portion may be configured to allow application of a partial vacuum to at least one of the cavities. With respect to the sharpened edge of the sheath portion it is generally preferred that the edge has an inside chamfer. In such configurations, it is particularly preferred that the inside chamfer will matingly engage with the thinner (typically angled) distal end.

In another especially preferred aspect, a biopsy device comprises a needle portion and a sheath portion that are configured and positioned relative to each other to allow simultaneous sectioning of a tissue to produce two tissue samples with corresponding surfaces using a motion of the needle portion relative to the sheath portion.

Most preferably, the needle portion in such devices comprises a closed incising tip that is configured as a chisel blade, and/or further includes two cavities on opposite sides of the needle portion that are positioned such that at least part of each cavity has the same distance from the tip. It is still further preferred that where the needle portion has a cavity and where the sheath portion includes a blade, the sheath portion and the needle portion are configured such that the blade can move along a longitudinal axis of the cavity as the sheath portion is moved relative to the needle portion.

Therefore, and viewed from a different perspective a method of facilitating or performing a biopsy will include a step of providing a biopsy device that includes a needle portion and a sheath portion, wherein the needle portion and the sheath portion are configured to allow simultaneous sectioning of a tissue to produce two tissue samples with corresponding surfaces using motion of the needle portion relative to the sheath portion. In a further step, a user is advised to advance the biopsy device to a target area and to move the needle portion in the target area relative to the sheath portion to so produce the two tissue samples.

In especially preferred methods, the needle portion has a closed incising tip that is configured as a chisel blade, and/or includes at least two cavities on opposite sides of the needle portion that are positioned such that at least part of two cavities have the same distance from the tip. It is further preferred that the needle portion is configured to allow application of a partial vacuum to at least one cavity in the needle portion, and/or that the sheath portion is moved in a rotational and a transverse movement. In further contemplated aspects, movement of the needle portion relative to the sheath portion is driven by an automated mechanism that is coupled to the needle portion and the sheath portion.

Various objects, features, aspects and advantages of the inventive subject matter will become more apparent from the following detailed description of preferred embodiments, along with the accompanying drawings in which like numerals represent like components.

BRIEF DESCRIPTION OF THE DRAWING

FIG. 4 is a schematic illustration of a yet another exemplary biopsy device according to the inventive subject matter.

FIG. 5 is a schematic illustration of an exemplary post-biopsy core splitting device according to the inventive subject matter.

DETAILED DESCRIPTION

The inventor has discovered that multiple biopsy cores with two or more corresponding tissue surfaces can be taken from the same area of interest without substantial compression or other distortion of the surfaces. Most preferably, contemplated methods and devices split the tissue first with a needle (e.g., via cutting or other physical separation) to thereby produce the corresponding surfaces that are then received in respective sample cavities. Most preferably, the cutting and receiving are performed in separate locations and as the needle travels through the tissue. The samples are then cut from the tissue using a second implement, and most typically a sheath that coaxially moves along the biopsy needle (wherein the movement may be transverse, or transverse and in a rotating manner). Alternatively, or additionally, the sheath may comprise a blade that (further) sections the tissue sample in the cavity or cavities. Thus, it is preferred that the devices according to the inventive subject matter will allow (simultaneous) sectioning of a tissue to produce two tissue samples with corresponding surfaces using a motion of the needle portion relative to the sheath portion. As used herein, the term "corresponding surfaces" refers to surfaces that are generated by cutting or tearing of a tissue. Therefore, corresponding surfaces will represent the same plane of the tissue through which the cut or tear propagated.

Consequently, it should be appreciated that especially preferred biopsy devices will have at least one needle portion and at least one sheath portion. The needle portion will typically have a closed incising tip and at least two cavities (preferably on opposite sides and positioned such that at least part of each cavity has the same distance from the tip), while the sheath portion will have a sharpened front edge that allows sectioning of respective tissue that is at least partially disposed in the two cavities.

Figure 1:
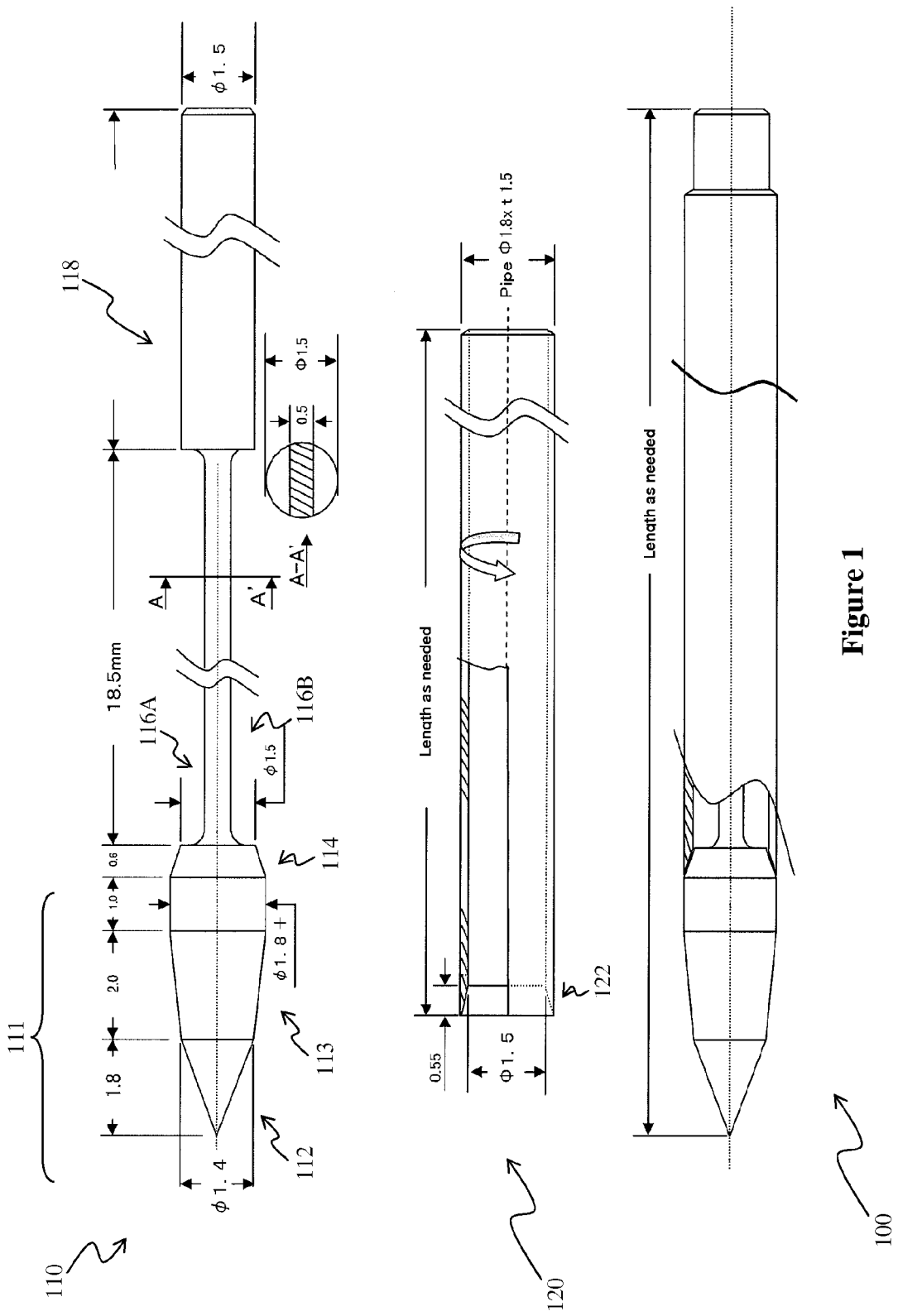
FIG. 1 is a schematic illustration of one exemplary biopsy device according to the inventive subject matter.

For example, in one preferred aspect of the inventive subject matter, a biopsy device has a configuration as schematically illustrated in FIG. 1 (here: exemplary dimensions indicated in millimeters, other dimensions also suitable), where the device 100 includes a needle portion 110 and a sheath portion 120. Most typically, the needle portion has a tip 111 with an incising proximal end 112 that is preferably formed as a chisel blade and a distal end 114 that preferably has a thinner cross section (e.g., via an angled portion relative to an axis parallel to the longitudinal axis of the needle portion). It is especially preferred that the distal end 114 is shaped such as to accommodate the sharpened end portion 122 of the sheath portion to thereby avoid formation of a transition between the sheath and the needle portion that would allow tissue to be cut by the sharpened end portion as the device is advanced to the target tissue. Most typically, the portion 113 that is located between the distal end and the proximal end of the tip is configured to allow further separation of the tissue incised by the proximal end. Therefore, the portion 113 will typically have an angled section (angle relative to an axis parallel to the longitudinal axis of the needle portion). However, it should be appreciated that a non-angled geometry is also contemplated, including rounded geometries.

Following the distal end, the needle portion includes at least one, and more typically two sample receiving cavities 116A and 116B. It is generally preferred that the needle portion 110 has at least one, and more typically at least two sample receiving cavities, where the two cavities have the same configuration and size, and are located in opposite positions and the same distance relative to the incising proximal end 112. Such configuration advantageously maximizes the areas of corresponding surfaces in the two or more samples obtained. Moreover, and particularly where the proximal end is configured as a chisel blade, it is preferred that the bases of the sample cavities are in a plane that is substantially parallel (deviation of no more than 20 degrees, and more typically no more than 10 degrees) to a plane drawn through the chisel blade (wherein that plane is also parallel to the longitudinal axis of the needle portion). Following the sample cavities in a direction away from the proximal end 112 is the remaining portion 118 of the needle portion that can extend to a length as required by the particular tissue to be sampled. It should be noted that the specific dimensions and configuration of that remaining portion 118 will predominantly be determined by the overall length of the needle portion and, if needed, type of biopsy gun employed. Therefore, the remaining end may further include one or more implements through which the biopsy device or needle portion may be attached to the biopsy gun (not shown).

In alternative aspects of the inventive subject matter, it is also contemplated that the incising proximal end 112 may be configured in various other geometries, and especially preferred geometries include point-shaped forms, and tips comprising triagonal or tetragonal (and higher) pyramidal shapes to so lead to the formation of three or four (or more) corresponding surfaces. Moreover, while it is generally preferred that the needle portion has an angled intermediate portion 113 that allows for further separation of the tissue after incision or splitting, such intermediate portion may be modified to lack an angled portion to have a curved portion, or may be omitted altogether. Similarly, the distal portion may be omitted or shaped in numerous alternative forms (e.g., curved, flat, stepped, etc.) to provide a corresponding fit or resting place for the sharpened end of the sheath portion, or even include a recess into which at least a portion of the sharpened end of the sheath portion may fit.

Consequently, it should be appreciated that the needle portion may comprise a single, more typically two, and in some cases three or more sample receiving cavities in the portion following the distal end of the tip. Depending on the particular geometry of the incising tip, the position of the cavities relative to each other may vary considerably. However, it is generally preferred that the bases of the cavities are substantially parallel to the corresponding surfaces of the tissue samples formed by the tip. Thus, the cavities are preferably at opposite sides of the needle or radially arranged. Similarly, it is generally preferred that at least two of the cavities at least partially overlap in their distance from the incising proximal end to so generate samples with corresponding tissue surfaces.

Figure 2:
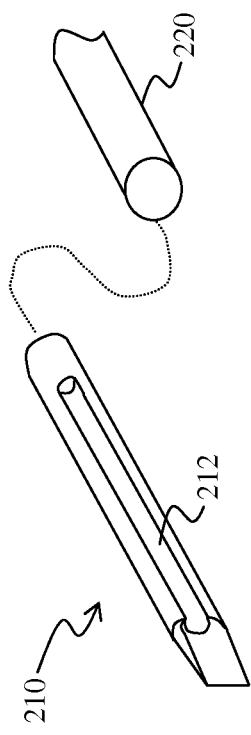
FIG. 2 is a schematic illustration of another exemplary biopsy device according to the inventive subject matter.

It is still further contemplated that at least two cavities of the needle portion may form a single larger cavity as exemplarily depicted in FIG. 2. Here, needle portion 210 has a cavity 212 with lateral openings that receive the corresponding surfaces generated by the incising tip. Once the tissue samples are in the respective cavities, the sheath 220 is moved towards the tip and the sharpened front edge will sever the samples from the tissue. In such embodiments (and the embodiments described above), it should be recognized that at least a portion of the needle portion is hollow or comprises a channel through which a partial vacuum (suction) can be applied to at least one of the cavities.

Figure 3:
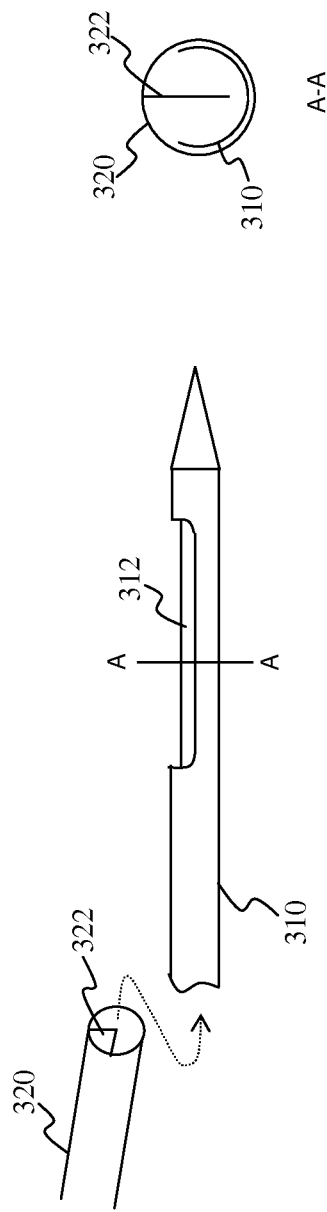
FIG. 3 is a schematic illustration of a further exemplary biopsy device according to the inventive subject matter.

Sheath portion 120 is preferably formed as a single tube or cylinder which slidingly fits over the needle portion and has a length that is sufficient to cover the sample cavities when the sheath portion is moved against the tip 111. Most typically, the sheath has a sharpened front edge 122 having a chamfered edge. It is generally preferred that the chamfer of the sharpened edge is on the inside of the sheath portion, however, an outside chamfer and a centrally beveled edge is also contemplated. In most preferred aspects, the chamfer is selected such that the sharpened edge matingly abuts the distal portion of the tip. Additionally, the sheath portion may be further configured to allow not only transverse motion along the longitudinal axis of the needle portion, but also rotational movement. To that end, the inner or outer surface of the sheath portion may comprise a rifling, or the sheath portion may be coupled to an implement that cooperates with a biopsy gun to provide a rotating motion to the sheath portion as the sheath portion slides along the needle portion.

Where desired, the sheath portion may also include one or more blades in the lumen of the sheath as exemplarily depicted in FIG. 3. Here, the sheath 320 has a sharpened front edge as discussed above, however, has an additional blade 322 that is configured to allow vertical section of a tissue sample that is collected in the sample receiving cavity 312 (or cavities). In such configurations, it should be noted that the needle portion will typically have a channel that accommodates movement of the blade for assembly of the biopsy device. Such channel is typically provided in the tip portion, however, other locations are also deemed suitable herein. Alternatively, the tip may be removed (or later formed) for assembly of the device.

It should be particularly appreciated that contemplated configurations and methods allow harvest of tissue samples with corresponding surfaces without generating tissue compression, drag, and shear, and therefore provide significantly improved samples that can be easily registered and analyzed. Moreover, contemplated devices and methods allow removal of the collected samples at the same time (rather than serial removal). Still further, as contemplated devices are similar in structure to single sample biopsy devices, contemplated devices can be readily adapted for use in currently known biopsy guns.

Alternatively, a cutting tool may be removably coupled to the sheath portion (or provided as a separate tool that comprises a sheath portion), wherein the cutting tool includes a blade that sections the tissue after removal from the patient while the tissue is still in the sample cavity of the needle portion. In most preferred aspects, the sheath or tool will have a guiding element (e.g., groove) that assists straight movement of the blade through the tissue. For example, FIG. 4 schematically illustrates a cutting tool 430 with a sheath 432 that has a moveable (small arrow) or insertable blade 434 which sections the sample in a side-cut needle. Alternatively, the blade may also be in a fixed position relative to the sheath portion, and the sheath portion is then moved relative to the needle portion 410 (large arrow). To even further reduce friction forces on the biopsy sample that is still in the sample cavity 412 of the needle portion, a rolling blade may be used.

In still further alternative aspects, the blade may be located in a position other than the tip portion. For example, the blade may be located in the proximal portion of the needle (relative to a handle or gun), wherein cutting may be performed during the sampling as the needle advances, and/or during core removal through the proximal portion. In still further alternative aspects, and especially where the needle is driven by a spring-loaded mechanism, the blade may also be replaced by one or more thin wires.

Suitable needles with blades or other cutting implements are preferably formed using a standard needle production process in which the blade is inserted into corresponding preformed cuts or indentations in the lumen of the needle body. Alternatively, modification kits are also contemplated in which a user adds the blade to an existing biopsy needle. Such kits may advantageously comprise a generally cylindrical sheath that is inserted into the existing biopsy needle, wherein the sheath has a blade or wire arrangement at or proximal to the end of the sheath. Alternatively, or additionally, the core may also be removed from a conventional needle by inserting the needle into a sheath that has a blade arrangement as discussed above, wherein the core is typically suctioned out of the needle through the blade.

FIG. 5 depicts one exemplary embodiment for such device and methods. Here, device 500 is configured to have a portion 510 that sealingly receives an open tip biopsy needle 520 in which a biopsy core 522 is located. Needle stop 512 is further included in portion 510. The device 500 further preferably includes an opening 530 that is sized and dimensioned to accommodate at least a portion of a blade (not shown) such that the blade can slice the core 522 as the core 522 is sucked through the device toward screen 540. Opening 550 is preferably configured to allow removal of the split cores, wherein the opening is typically sealed by a sleeve 560 or plug (not shown). Where a sleeve is used, the sleeve may include a window 562 that corresponds to the opening 550 to so allow removal of the split cores. The sleeve is then rotated to close the opening 550 prior to next use. Alternatively, the blade may form part of the device 500, and may be configured in numerous manners (e.g., linear blade, cutting wire, etc. In especially preferred devices, the blade or opening is disposed in a portion of the device that has a larger inner diameter than the diameter of the biopsy core to accommodate for the added cross sectional profile due to the blade width. Of course, it should be appreciated that the width is not too wide to so prevent collapse of the partial vacuum. Air is evacuated from the device 500 via suction port 514. Where desirable, the blade 540 may be coupled to a device that imparts vibrating or other motion to facilitate cutting (not shown).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The invention claimed is:

1. A method of performing a biopsy with a biopsy device, the biopsy device comprising a needle portion having an incising proximal end and first and second cavities, wherein the incising proximal end has a closed incising tip forming a blade surface shaped to form a cutting plane through the tissue, and the biopsy device further comprising sheath portion having a sharpened front edge, wherein the sheath portion at least partially surrounds the needle portion, the method comprising the steps of:
   advancing the needle portion into a tissue to produce simultaneously first and second tissue portions with first and second surfaces facing with each other along a plane of sectioning;
   further advancing the needle portion such that the first and second cavities receive the first and second tissue portion, wherein the first and second surfaces face respective bases of the first and second cavities;
   advancing the sheath portion relative to the needle portion such that the first and second tissue portions are cut from the tissue by the sharpened front edge while the first and second tissue surfaces are retained in the first cavity and second cavity; and
   wherein the bases of the first and second cavities are in respective planes that are equidistant and substantially parallel to the cutting plane to allow removal of a plurality of biopsy cores with corresponding tissue surfaces from the same area of interest without compression or distortion of the surfaces.

2. The method of claim 1, wherein first cavity and the second cavity are on opposite sides of the needle portion and are positioned such that at least part of each cavity has the same distance from the tip.

3. The method of claim 1, wherein the needle portion is configured to allow application of a partial vacuum to at least one of the first and second cavities.

4. The method of claim 1, wherein advancing the sheath portion comprises a rotational and a transverse movement of the sheath portion.

5. The method of claim 1, wherein advancing sheath portion relative to the needle portion is performed using a biopsy gun.

6. A method of performing a biopsy, comprising:
   providing a biopsy device having a needle portion and a sheath portion;
   wherein the needle portion has a first cavity, a second cavity, and a closed incising tip forming a blade surface shaped to form a cutting plane through the tissue, and a distal end;
   wherein the bases of the first and second cavities are in respective planes that are equidistant and substantially parallel to the cutting plane to allow removal of a plurality of biopsy cores with corresponding tissue surfaces from the same area of interest without compression or distortion of the surfaces;
   wherein the needle portion and the sheath portion are configured to allow sectioning of a tissue to simultaneously produce first and second tissue portions with corresponding surfaces facing each other along a plane of sectioning using motion of the needle portion relative to the sheath portion;
   instructing a user to advance the biopsy device to a target area, to incise the tissue along the plane of sectioning in the target area, and to move the needle portion in the target area relative to the sheath portion to collect the first and second tissue portions into first and second cavities in the needle portion, wherein respective bases of the first and second cavities are in a plane that is substantially parallel to the surfaces of the corresponding surfaces.

7. The method of claim 6, wherein the first and second cavities are on opposite sides of the needle portion and are positioned such that at least part of each cavity has the same distance from the tip.

8. The method of claim 6, wherein the needle portion is configured to allow application of a partial vacuum to at least one of the first and second cavities.

9. The method of claim 6, wherein moving the sheath portion comprises a rotational and a transverse movement of the sheath portion.

10. The method of claim 6, wherein moving the needle portion relative to the sheath portion is performed using a biopsy gun.

11. A biopsy device comprising:
a needle portion having an incising proximal end forming a blade surface shaped to form a cutting plane through the tissue, and having first and second cavities;
a sheath portion having a sharpened front edge;
wherein the incising proximal end is part of a closed incising tip, and is configured to incise the tissue along the cutting plane to form corresponding first and second tissue portions with respective first and second tissue surfaces;
wherein the bases of the first and second cavities are in respective planes that are equidistant and substantially parallel to the cutting plane to allow removal of a plurality of biopsy cores with corresponding tissue surfaces from the same area of interest without compression or distortion of the surfaces;
wherein the corresponding tissue surfaces face each other along the cutting plane;
wherein the first and second cavities are positioned on opposite sides and are configured to receive the first and second tissue portions;
wherein the bases of the first and second cavities are in a plane that is substantially parallel to first and second tissue surfaces; and
wherein the sheath portion is movably coupled to the needle portion such that the first and second tissue portions are cut from the tissue by the sharpened front edge while the first and second tissue portions are retained in the first and second cavities.

12. The biopsy device of claim 11, wherein at least 70% of a length of the first and second cavities have the same distance from the incising proximal end.

13. The biopsy device of claim 11, wherein the first and second cavities form a contiguous opening through the needle portion.

14. The biopsy device of claim 11, wherein the needle portion further comprises third and fourth cavities on opposite sides.

15. The biopsy device of claim 11, wherein the needle portion is further configured to allow application of a partial vacuum to at least one of the first and second cavities.

\* \* \* \* \*